United States Patent [19]

Licciardello et al.

[11] Patent Number: 4,543,203
[45] Date of Patent: Sep. 24, 1985

[54] 2-ISOPROPENYL-1,5-DIMETHYL-CYCLO-PENTANE CARBOXALDEHYDE

[75] Inventors: Michael Licciardello, Little Silver; Richard M. Boden, Ocean, both of N.J.

[73] Assignee: International Flavors & Fragrances Inc., New York, N.Y.

[21] Appl. No.: 609,346

[22] Filed: May 11, 1984

Related U.S. Application Data

[62] Division of Ser. No. 474,018, Mar. 10, 1983, Pat. No. 4,474,992.

[51] Int. Cl.$^4$ ................................................ C11B 9/00
[52] U.S. Cl. .......................... 252/522 R; 252/522 A; 252/8.6; 252/174.11; 424/69; 424/70; 424/71; 514/844; 514/881
[58] Field of Search ................ 252/522 R, 522 A, 8.6, 252/174.11; 424/69, 70, 71

[56] References Cited

U.S. PATENT DOCUMENTS

| | | | |
|---|---|---|---|
| 3,937,723 | 2/1976 | Schulte-Elte | 252/522 R X |
| 3,963,675 | 6/1976 | Naegeli | 252/522 R X |
| 4,283,561 | 8/1981 | Hagen et al. | 252/522 R X |

FOREIGN PATENT DOCUMENTS

| | | | |
|---|---|---|---|
| 7313419 | 4/1974 | Netherlands | 252/522 R |
| 604714 | 9/1978 | Switzerland | 252/522 R |

*Primary Examiner*—Thomas A. Waltz
*Attorney, Agent, or Firm*—Arthur L. Liberman

[57] ABSTRACT

Described is 2-isopropenyl-1,5-dimethyl-cyclopentane carboxaldehyde of our invention having the structure:

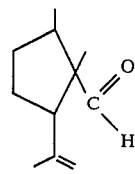

and uses thereof for augmenting or enhancing the aroma of perfumes, colognes and perfumed articles including solid or liquid anionic, cationic, nonionic or zwitterionic detergents, perfumed polymers, fabric softener compositions, fabric softener articles including drier-added fabric softener articles, hair preparations, cosmetic powders, face creams, moisturizers and the like. Also described is a process for preparing 2-isopropenyl-1,5-dimethyl-cyclopentane carboxaldehyde of our invention according to the reaction:

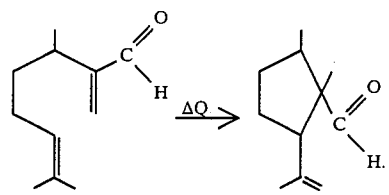

5 Claims, 3 Drawing Figures

FIG.I
GLC PROFILE FOR EXAMPLE I.
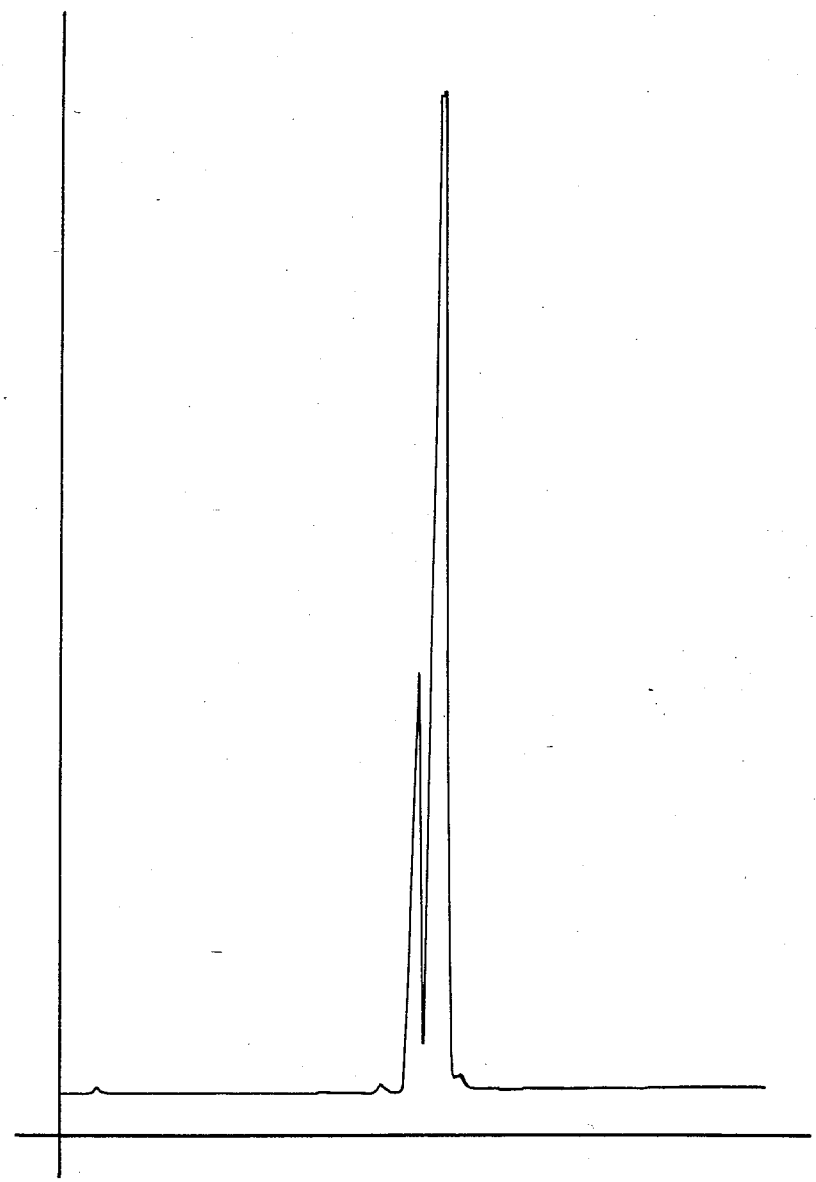

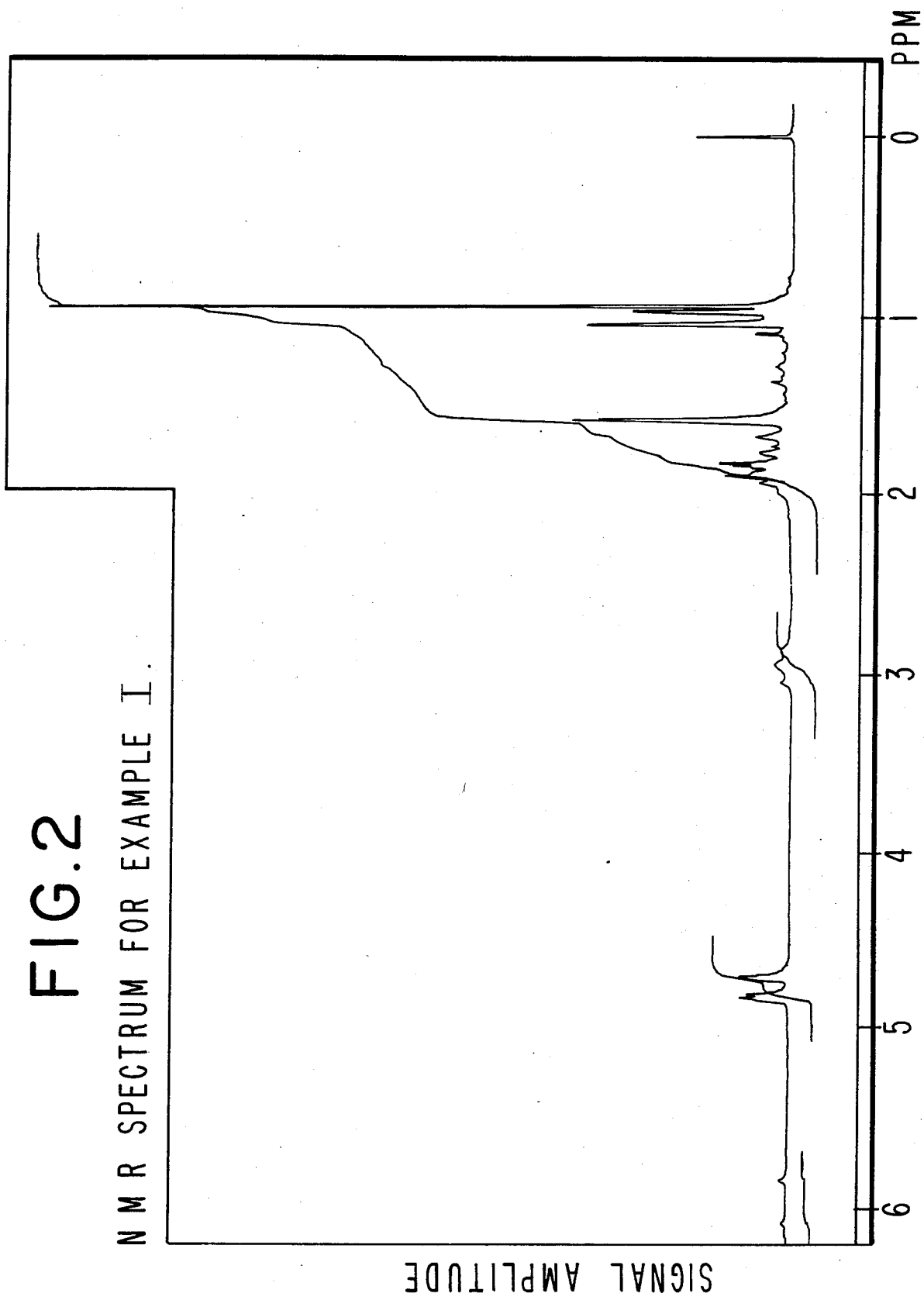
FIG. 2 NMR SPECTRUM FOR EXAMPLE I.

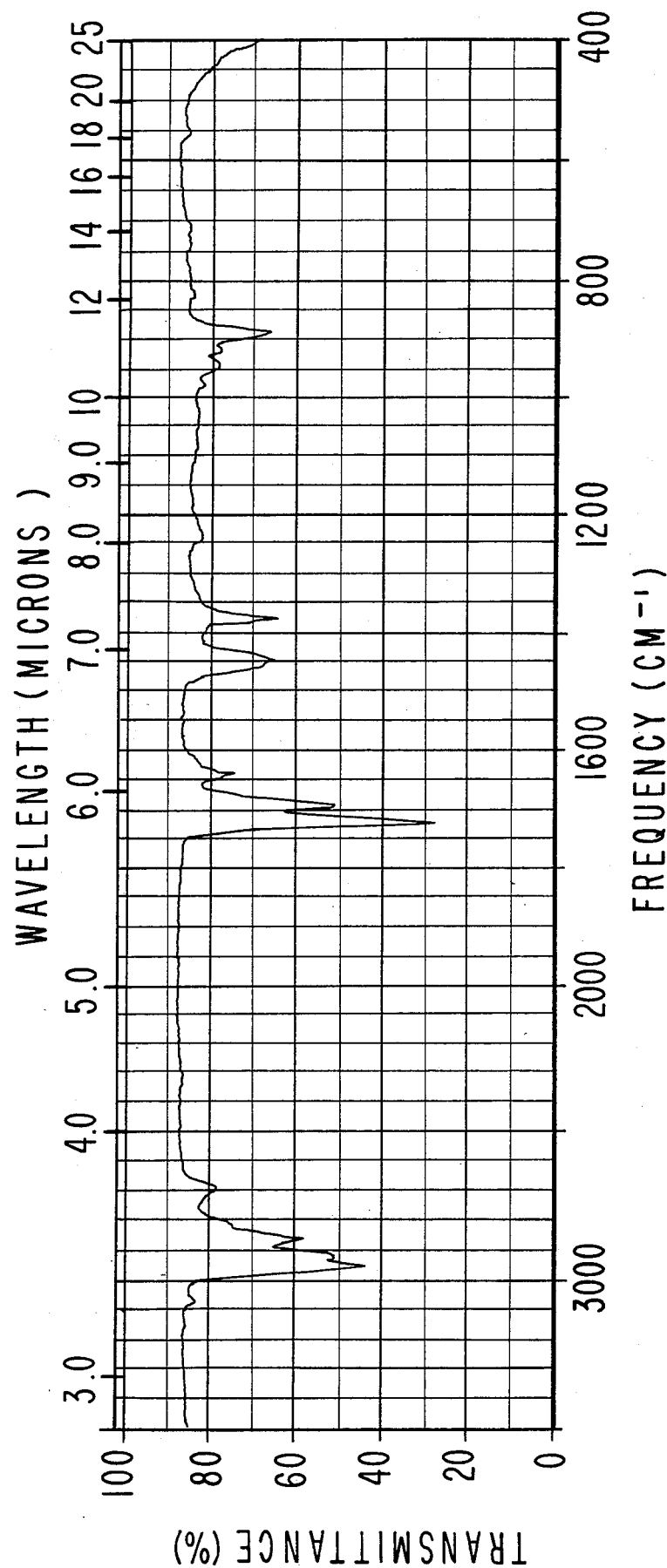

2-ISOPROPENYL-1,5-DIMETHYL-CYCLOPENTANE CARBOXALDEHYDE

This is a divisional of application Ser. No. 474,018, filed Mar. 10, 1983 now U.S. Pat. No. 4,474,992 issued on Oct. 2, 1984.

BACKGROUND OF THE INVENTION

The present invention provides the novel 2-isopropenyl-1,5-dimethyl-cyclopentanecarboxaldehyde of our invention having the structure:

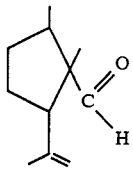

and uses thereof in augmenting or enhancing the aroma of consumable materials.

Materials which can provide lavender, camphoraceous, patchouli, eucalyptus, rosemary, minty and floral aroma nuances are well known in the art of perfumery. Many of the natural substances which provide such fragrances and contribute the desired nuances to perfumery compositions are high in cost, vary in quality from one batch to another and/or are generally subject to the usual variations of natural products.

The prior art contains a large number of teachings regarding the use of organic aldehydes in augmenting or enhancing the aroma of perfumes. Thus, U.S. Pat. No. 3,463,818 relates to a process for producing alpha methylene and alpha methyl aldehydes useful as perfumes. U.S. Pat. No. 3,463,818, the disclosure of which is incorporated by reference herein, specifically discloses the production and perfumery use of the compound 3,7-dimethyl-2-methylene-6-octenol having the structure:

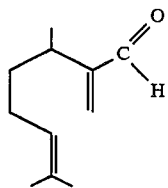

which is the precursor of the 2-isopropenyl-1,5-dimethyl-cyclopentane carboxaldehyde of our invention having the structure:

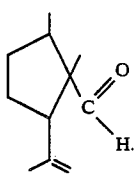

The properties 2-isopropenyl-1,5-dimethyl-cyclopentane carboxaldehyde having the structure:

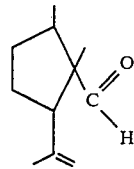

from an organoleptic standpoint are different *in kind* from the properties of the compound having the structure:

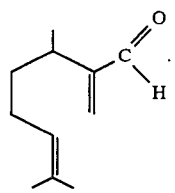

BRIEF DESCRIPTION OF THE DRAWINGS

FIG. 1 is the GLC profile for Fraction 5 of the distillation product of the reaction product of Example I consisting of the compound having the structure:

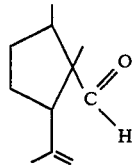

FIG. 2 is the NMR spectrum for the compound having the structure:

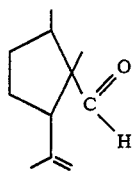

produced according to Example I (Conditions: Field strength 100 MHz; solvent $CFCl_3$).

FIG. 3 is the infra-red spectrum for the compound having the structure:

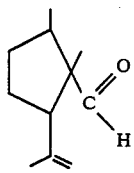

produced according to Example I.

THE INVENTION

The present invention provides the compound, 2-isopropenyl-1,5-dimethyl-cyclopentane carboxaldehyde having the structure:

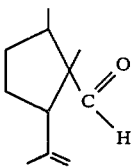

The present invention also provides an economical efficient process for synthesizing 2-isopropenyl-1,5-dimethyl-cyclopentane carboxaldehyde having the structure:

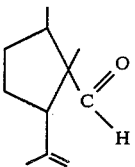

by pyrolizing the aldehyde having the structure:

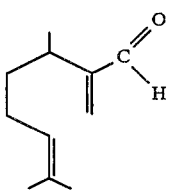

according to the reaction:

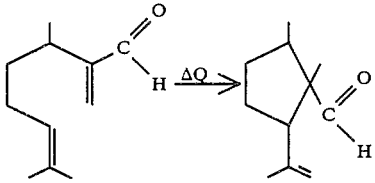

The present invention also provides processes for using 2-isopropenyl-1,5-dimethyl-cyclopentane carboxyaldehyde having the structure:

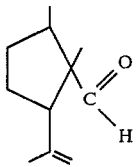

for its organoleptic properties in augmenting or enhancing the organoleptic properties of consumable materials, that is, the aroma of perfumes, colognes and perfumed articles (such as perfumed polymers, solid or liquid cationic, anionic, nonionic or zwitterionic detergents, soaps, fabric softener compositions, drier-added fabric softener articles such as "BOUNCE ®" registered trademark of the Procter & Gambler Company of Cincinnati, Ohio, fabric brighteners, cosmetic powders, bath preparations, hair preparations such as hair sprays and shampoos).

The 2-isopropenyl-1,5-dimethyl-cyclopentane carboxaldehyde of our invention may be prepared by carrying out the pyrolysis of the compound having the structure:

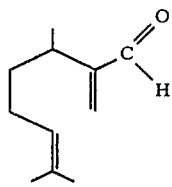

at a temperature in the range of from about 425° C. up to about 530° C. The pressure of the reaction may vary from subatmospheric, e.g., 0.5 atmospheres, to supra, atmospheric, e.g., 10 atmospheres. The most convenient and practical pyrolysis pressure to carry out the reaction is 1 atmosphere. The time of reaction or residence time of the reaction mass during the pyrolysis may vary from about 10 seconds up to about 4 minutes. The process is carried out, preferably, in a quartz tubular pyrolysis reactor in the presence of an inert gas, preferably nitrogen. The concentration of the aldehyde having the structure:

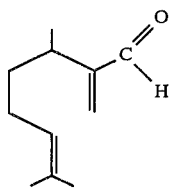

in the gas stream may vary from 100 percent (in the absence of nitrogen diluent) down to about 40 percent (molar concentration).

The crude reaction mass is then distilled using a fractional distillation column at temperatures, for example, in the range of 56°-58° C. and a vacuum of 1.8 mm. Hg pressure.

The 2-isopropenyl-1,5-dimethyl-cyclopentane carboxaldehyde of our invention can be used to contribute lavender, camphoraceous, patchouli, eucalyptus, rosemary, minty and floral aroma nuances to perfume compositions, colognes and perfumed articles such as solid or liquid cationic, anionic, nonionic or zwitterionic detergents, perfumed polymers, fabric softener compositions, fabric softener articles, optical brighteners, fabric conditioners, hair preparations, shampoos and hair sprays. As an olfactory agent, the 2-isopropenyl-1,5-dimethyl-cyclopentane carboxaldehyde of our invention can be formulated into or used as a component of a "perfume composition".

The term "perfume composition" is used herein to mean a mixture of organic compounds including, for example, alcohols, aldehydes, ketones, nitriles, ethers, lactones, esters other than the carbonate of our invention, and frequently hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) top notes which are usually low-boiling, fresh-smelling materials.

In perfume compositions, the individual component will contribute its particular olfactory characteristics, but the overall effect of the perfume composition will be the sum of each of the effects of each of the ingredients. Thus, the individual compounds of this invention or mixtures thereof can be used to alter the aroma characteristics of the perfume composition, for example, by highlighting or moderating the olfactory reaction contributed by another ingredient in the composition.

The amount of 2-isopropenyl-1,5-dimethyl-cyclopentane carboxaldehyde of our invention which will be effective in perfume compositions depends upon many factors including the other ingredients, their amounts and the effects which are desired. It has been found that perfume compositions containing as little as 0.1 percent of the 2-isopropenyl-1,5-dimethyl-cyclopentane carboxaldehyde of our invention or even less and perfume compositions containing as much as 70 percent of the 2-isopropenyl-1,5-dimethyl-cyclopentane carboxaldehyde of our invention can be used to impart interesting lavender, camphoraceous, patchouli, eucalyptus, rosemary, minty and floral aromas to perfumed articles, perfume compositions and colognes. Such perfumed articles include fabric softener compositions, drier-added fabric softener articles, cosmetic powders, talcs, solid or liquid anionic, cationic, nonionic or zwitterionic detergents and perfumed polymers. The amount employed can range up to 70 percent and will depend on considerations of cost, nature of the end product and the effect desired on the finished product and particular fragrance sought.

Thus, 2-isopropenyl-1,5-dimethyl-cyclopentane carboxaldehyde of our invention can be used alone or in a perfume composition as an olfactory component, in solid or liquid anionic, cationic, nonionic or zwitterionic detergents (including soaps), perfumed polymers (those which may be microporous, those which are macroporous and may contain, if desired, particulate absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer or a polymer containing an absorbent filler or a perfumed article such as a solid or liquid cationic, anionic, nonionic or zwitterionic detergent or a cosmetic powder, as little as 0.01 percent of the 2-isopropenyl-1,5-dimethyl-cyclopentane carboxaldehyde of our invention will suffice to provide an interesting lavender, camphoraceous, patchouli, eucalyptus, rosemary, minty and floral aroma profile. Generally, no more than 0.8 percent of the 2-isopropenyl-1,5-dimethyl-cyclopentane carboxaldehyde of our invention is required in the perfumed article. Accordingly, the range of 2-isopropenyl-1,5-dimethyl-cyclopentane carboxaldehyde in perfumed articles for the purposes of our invention is from about 0.01 percent up to about 0.8 percent.

In addition, the perfume composition of our invention can contain a vehicle or carrier for the 2-isopropenyl-1,5-dimethyl-cyclopentane carboxaldehyde of our invention alone or with other ingredients. The vehicle can be a liquid such as an alcohol such as ethanol, glycol such as propylene glycol or the like. The carrier can be an absorbent solid such as a gum (e.g., xanthan gum or gum arabic) or components for encapsulating the composition as by coacervation (using gelatin) or by forming a polymer wall around a liquid center, e.g., using a urea formaldehyde prepolymer to form a polymeric wall around the liquid perfume center.

When incorporating the 2-isopropenyl-1,5-dimethyl-cyclopentane carboxaldehyde of our invention into polymers, various techniques well known to those skilled in the art may be used. Thus, the 2-isopropenyl-1,5-dimethyl-cyclopentane carboxaldehyde of our invention may be admixed with a molten polymer such as polyethylene or polypropylene and the resulting mixture may be formed into pellets which are used as a polymer concentrate. In the alternative, the 2-isopropenyl-1,5-dimethyl-cyclopentane carboxaldehyde of our invention taken alone or further in combination with other perfume ingredients may be blended into a polymer during an extrusion operation using a single screw or twin screw extruder. When using an extruder polymers of ethylene, propylene, ethylene/vinyl acetate copolymers and poly(epsilon caprolactone) as well as various nylons, e.g., nylon-6.

The following Example I sets forth the process for preparing the 2-isopropenyl-1,5-dimethyl-cyclopentane carboxaldehyde of our invention. The following Example II, et seq. represent methods for using the 2-isopropenyl-1,5-dimethyl-cyclopentane carboxaldehyde of our invention for its organoleptic properties.

Unless otherwise indicated, all parts and percentages are by weight.

EXAMPLE I

Preparation of 2-isopropenyl-1,5-dimethyl-cyclopentane Carboxaldehyde

Reaction:

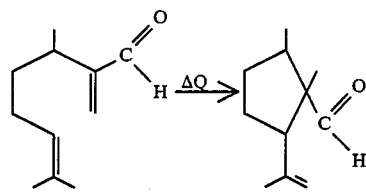

The compound having the structure:

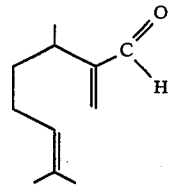

is passed through a 1" diameter quartz tube heated using an electrical induction heater and a temperature profile at four points in the quartz tube space 3" apart of:

| | |
|---|---|
| Location 1 | 425° C. |
| Location 2 | 460° C. |
| Location 3 | 500° C. |

-continued

| Location 4 | 529° C. | at a rate of 3 ml per minute (total 600 grams) and in the presence of nitrogen the ratio of compound having the structure:

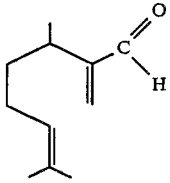

to nitrogen being 3:10.

The resulting product is distilled on a spinning band column to yield the following fractions:

| Fraction No. | Vapor Temp. (°C.) | Liquid Temp. (°C.) | Vacuum mm/Hg. Pressure |
|---|---|---|---|
| 1 | /54 | /80 | /1.0 |
| 2 | 60 | 87 | 1.0 |
| 3 | 62 | 92 | 1.0 |
| 4 | 64 | 96 | 1.0 |
| 5 | 80 | 155 | 1.0 |

Fractions 1 to 5 are bulked and redistilled to yield the following fractions:

| Fraction No. | Vapor Temp. (°C.) | Liquid Temp. (°C.) | Vacuum mm/Hg. Pressure | Reflux Ratio |
|---|---|---|---|---|
| 1 | 38/58 | 89/90 | 2.2/1.8 | 4:1/4:1 |
| 2 | 58 | 83 | 1.8 | 4:1 |
| 3 | 58 | 93 | 1.8 | |
| 4 | 56 | 98 | 1.8 | 4:1 |
| 5 | 56 | 104 | 1.8 | 4:1 |
| 6 | 58 | 108 | 1.8 | 4:1 |
| 7 | 60 | 112 | 2.0 | 4:1 |
| 8 | 50 | 130 | 1.9 | 4:1 |
| 9 | 53 | 133 | 1.9 | 4:1. |

FIG. 1 is the GLC profile for Fraction 5 of the immediately preceeding distillation.

FIG. 2 is the NMR spectrum for the compound having the structure:

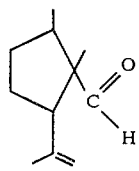

(Conditions: Field strength 100 MHz, 70: Solvent: CFCl₃).

FIG. 3 is the infra-red spectrum for the compound having the structure:

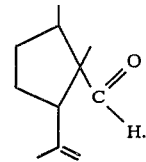

EXAMPLE II

Herbal Fragrance Formulation Produced Using the Product Prepared According to Example I

| Ingredients | Parts by Weight |
|---|---|
| Amyl cinnamic aldehyde | 20 |
| Phenyl acetaldehyde dimethyl acetal | 4 |
| Thyme oil white | 8 |
| Sauge sclaree French | 8 |
| Galbanum oil | 4 |
| Juniper berry oil | 10 |
| Methyl octin carbonate | 4 |
| Linalyl acetate | 2 |
| Dihydro methyl jasmonate | 10 |
| 2-Isopropenyl-1,5-dimethyl-cyclopentane carboxaldehyde having the structure: | 10 |

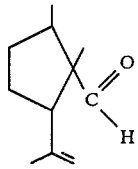

prepared according to
Example I, bulked
redistillation fractions 2-9

The 2-isopropenyl-1,5-dimethyl-cyclopentane carboxaldehyde prepared according to Example I adds a strong lavender, camphoraceous, patchouli, eucalyptus, rosemary, minty and floral undertone to this herbal fragrance formulation causing it to be more "rain forest-/natural-like".

EXAMPLE III

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| 2-Isopropenyl-1,5-dimethyl-cyclopentane carboxaldehyde prepared according to Example I, bulked fractions 2-8. | A lavender, camphoraceous, patchouli, eucalyptus-like, rosemary-like, minty and floral aroma. |
| Perfume compositions of Example II. | A fresh green, herbal aroma with lavender, camphoraceous, patchouli, eucalyptus, rosemary, minty and floral undertones and having a "fresh natural, tropical rain forest" aroma. |

EXAMPLE V

Preparation of Colognes and Handkerchief Perfumes

Compositions as set forth in Table I of Example III are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III are imparted to the colognes and to the handkerchief perfumes at all levels indicated.

EXAMPLE VI

Preparation of Soap Compositions

One hundred trams of soap chips (per sample) (IVORY ®. produced by the Procter & Gamble Company of Cincinnati, Ohio), are each mixed with one gram samples of substances as set forth in Table I of Example III until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III.

EXAMPLE VII

Preparation of Solid Detergent Compositions

Detergents are prepared using the following ingredients according to Example I of Canadian Pat. No. 1,007,948 (incorporated by reference herein):

| Ingredient | Percent by Weight |
| --- | --- |
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example III. Each of the detergent samples has an excellent aroma as indicated in Table I of Example III.

EXAMPLE VIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
57% $C_{20-22}$ HAPS
22% isopropyl alcohol
20% antistatic agent
1% of one of the substances as set forth in Table I of Example III.

Fabric softening compositions prepared according to Example I at column 15 of U.S. Pat. No. 3,632,396 having aroma characteristics as set forth in Table I of Example III supra, consist of a substrate coating having a weight of about 3 grams per 100 square inches of substrate; a first coating liquid directly on the substrate coating consisting of about 1.85 grams per 100 square inches of substrate; and an outer coating coated on the first coating consisting of about 1.4 grams per 100 square inches of substrate. One of the substances of Table I of Example III is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table I of Example III, supra.

EXAMPLE IX

Hair Spray Formulations

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 grams of the polymer is dissolved in the alcohol. The following ingredients are added to the PVP/VA alcoholic solution:

| | |
| --- | --- |
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example III | 0.10 weight percent |

The perfuming substances as set forth in Table I of Example III add aroma characteristics as set forth in Table I of Example III which are rather intense and aesthetically pleasing to the users of the soft-feel, good-hold pump hair sprays.

EXAMPLE X

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat ®755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table I of Example III is added to the mixture. The resulting mixture is cooled to 40° C. and blending is carried out for an additional one hour in each case. At the end of this blending period, the resulting material has a pleasant fragrance as indicated in Table I of Example III.

What is claimed is:

1. A process for augmenting or enhancing the aroma of a consumable material selected from the group consisting of perfume compositions, colognes and perfumed articles comprising the step of intimately admixing with said consumable material, an aroma augmenting or enhancing quantity of 2-isopropenyl-1,5-dimethyl-cyclopentane carboxaldehyde defined according to the structure:

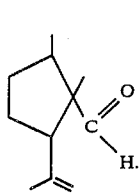

2. The process of claim 1 wherein the consumable material is a perfumed article and the perfumed article is a solid or liquid anionic, cationic, nonionic or zwitterionic detergent.

3. The process of claim 1 wherein the consumable material is a perfume composition or cologne.

4. The process of claim 1 wherein the consumable material is a perfumed article and the perfumed article is a fabric softener composition or fabric softener article.

5. The process of claim 1 wherein the consumable material is a perfumed polymer.

* * * * *